United States Patent [19]
Tabuchi et al.

[11] Patent Number: 6,033,798
[45] Date of Patent: *Mar. 7, 2000

[54] METHOD FOR PREDICTING DISCHARGE CAPACITY AND OPERATING VOLTAGE OF LITHIUM RECHARGEABLE BATTERY USING LITHIUM MANGANESE SPINEL CATHODE MATERIAL

[75] Inventors: Mitsuharu Tabuchi; Kazuaki Ado; Hiroyuki Kageyama; Osamu Nakamura, all of Ikeda, Japan

[73] Assignee: Agency of Industrial Science & Technology, Tokyo, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/769,526

[22] Filed: Dec. 19, 1996

[30] Foreign Application Priority Data

Dec. 22, 1995 [JP] Japan .................................. 7-350112

[51] Int. Cl.$^7$ .................................................. H01M 10/48
[52] U.S. Cl. .................................................. 429/90; 429/10
[58] Field of Search .................................. 429/10, 90, 91

[56] References Cited

PUBLICATIONS

B.D. Cullity, "Introduction to Magnetic Materials", Addison–Wesley Publishing, pp. 117–135. (no month available), 1972.

C. Masquelier et al., J. of Solid State Chemistry, vol. 123, pp. 255–266 (1996); "Chemical and Magnetic Characterization of Spinel Materials in the $LiMn_2O_4$–$Li_2Mn_4O_9$–$Li_4Mn_5O_{12}$ System" (no month available).

*Primary Examiner*—Maria Nuzzolillo
*Assistant Examiner*—Carol Chaney
*Attorney, Agent, or Firm*—Nikaido Marmelstein Murray & Oram, LLP.

[57] ABSTRACT

A method of determining the charge and/or discharge capacities of non-aqueous batteries with an operating voltage of about 4 volts, is provided including determining an inverse molar susceptibility value at each of a plurality of different temperatures for a plurality of lithium manganese spinel oxide cathode materials having different respective Mn valencies; plotting the inverse molar susceptibility values against temperatures for each of the plurality of lithium manganese spinel oxide cathode materials; determining values of at least one of two paramagnetic parameters, Weiss temperature and effective magnetic moment, by obtaining the temperature dependence of the above inverse molar susceptibility from a plot derived from the Curie-Weiss law, the Weiss temperature corresponding to a temperature value extrapolated to a zero point of the inverse molar susceptibility and the effective magnetic moment being obtainable from the gradient value of the plot; producing plural rechargeable lithium batteries in which lithium manganese spinel oxides with well-defined Mn valencies are used as cathode materials, and finding at least one of the charge or discharge capacities around 4V for each of the batteries; providing at least one correlation curve between the above-found charge and/or discharge capacities and the above-found at least one paramagnetic parameter value; and obtaining charge and/or discharge capacities for a rechargeable lithium battery containing a lithium manganese spinel oxide whose charge and/or discharge capacities are being sought from the at lest one determined paramagnetic parameter value using the at least one correlation curve. A method of determining the charge and/or discharge capacities of non-aqueous batteries with an operating voltage of about 4 volts, is also provided which includes determining a spontaneous magnetization value for each of a plurality of lithium manganese spinel oxide cathode materials having a different respective Mn valency by determining a magnetization value of each of a plurality of magnetic fields at a constant temperature to obtain and thereafter use a correlation curve.

4 Claims, 9 Drawing Sheets charge and discharge capacity (mAh/g)

METHOD FOR PREDICTING DISCHARGE CAPACITY AND OPERATING VOLTAGE OF LITHIUM RECHARGEABLE BATTERY USING LITHIUM MANGANESE SPINEL CATHODE MATERIAL

BACKGROUND OF THE INVENTION

This invention relates to a method for evaluating a lithium manganese spinel material which is a cathodes material of a lithium rechargeable battery.

At the present time, a lithium transitional metal oxide (such as $LiCoO_2$ or $LiNiO_2$) has been developed and used as a cathode material for a lithium ion battery utilized in portable equipment, and a lithium manganese spinel, such as $LiMn_2O_4$, has drawn attention as an advanced, low-cost, 4 V-grade cathode material and is currently under research and development.

The operating voltage and charge and discharge capacities of lithium batteries using this material is very sensitive mainly to the valency and distribution of Mn ion in the crystal structure. This means that properties of lithium ion batteries vary greatly depending upon conditions for the production of a powder for a cathode material, posing a serious problem associated with the stabilization of the quality of the batteries. Further, a lot of time is required for the evaluation in charge and discharge tests, and an anode should be combined with an electrolyte to constitute a cell.

Thus, the development of a method for evaluating a material for a cathode material, which, after the production of a cathode material powder, can rapidly predict the properties of a battery by a powder evaluation method sensitive to the distribution and valency of Mn ion and the like, has been earnestly desired for the development of cathode materials and the stabilization of the quality of the battery.

SUMMARY OF THE INVENTION

A primary object of this invention is to establish a suitable characterization method of cathode material like lithium manganese oxide spinels for predicting promptly the charge and discharge capacities and operating voltage of a lithium ion battery, using the magnetic measurement sensitive to the valency and distribution of Mn ion.

In view of the above problems of the prior art, the present inventors have made extensive and intensive studies and, as a result, have found that, in a lithium manganese oxide, one of lithium transition metal oxides which is a cathode material for a lithium ion battery, there is a close relationship between the magnetic properties and the charge and discharge capacities and the operating voltage, which had led to the completion of the present invention.

Accordingly, an object of the present invention is to provide a method for evaluating the following lithium manganese spinel oxide as a cathode material for a lithium ion battery.

According to the present invention, there is provided a first means for attaining the above object, that is, a method for predicting the charge and discharge capacities and the operating voltage of a lithium rechargeable battery using a lithium manganese spinel cathode material, wherein at least one magnetic parameter selected from an effective magnetic moment and a Weiss temperature provided by analyzing measured data on the temperature dependence of the magnetic susceptibility of the lithium manganese spinel cathode material is used to predict at least any one of charge and discharge capacities and an operating voltage in the case of use of the lithium manganese spinel cathode material as a cathode for a lithium rechargeable battery.

According to a preferred embodiment of the prediction method of the present invention, a correlation between at least any one value of the effective magnetic moment and Weiss temperature of a lithium manganese spinel cathode material with the valency of Mn being known and the charge and discharge capacities and operating voltage in the case of use of the lithium manganese spinel cathode material, with the valency of Mn being known, as the cathode for a lithium rechargeable battery is determined, at least any one value of the effective magnetic moment and Weiss temperature of a lithium manganese spinel cathode material with the valency of Mn being unknown is determined and at least any one of charge and discharge capacities and an operating voltage is predicted from the determined value based on the correlation provided for the lithium manganese spinel cathode material with the valency of Mn being known.

The effective magnetic moment is also influenced by the lattice volume of the spinel. Therefore, when the relationship between the magnetic parameter and the performance of the battery is determined and when the performance of the battery is predicted, using this relationship, from an unknown cathode material, it is preferred to always determine the lattice volume of Mn by X-ray diffractometry.

According to the present invention, there is provided a second means for attaining the above object, that is, a method for predicting the charge and discharge capacities and the operating voltage of a lithium rechargeable battery using a lithium manganese spinel cathode material, wherein spontaneous magnetization provided by analyzing measured data of the dependency of the magnetization of the lithium manganese spinel cathode material at a low temperature upon the magnetic field and the temperature is used to predict at least any one of charge and discharge capacities and an operating voltage in the case of use of this material.

According to a preferred embodiment of the prediction method of the present invention, a correlation between the spontaneous magnetization of a lithium manganese spinel cathode material with the valency of Mn being known and at least any one of the charge and discharge capacities and operating voltage in the case of use of the known lithium manganese spinel cathode material as the cathode for a lithium rechargeable battery is determined, spontaneous magnetization of a lithium manganese spinel cathode material with the valency of Mn being unknown is determined and at least any one of charge-and discharge capacities and an operating voltage in the case of use of the unknown lithium manganese spinel material as a cathode for a lithium rechargeable battery is predicted from the determined value.

According to the above prediction method, it is also possible to predict the capacity at a particular voltage on a charge and discharge curve, for example, in a particular voltage region around 4 V or 3 V.

Figure 4:
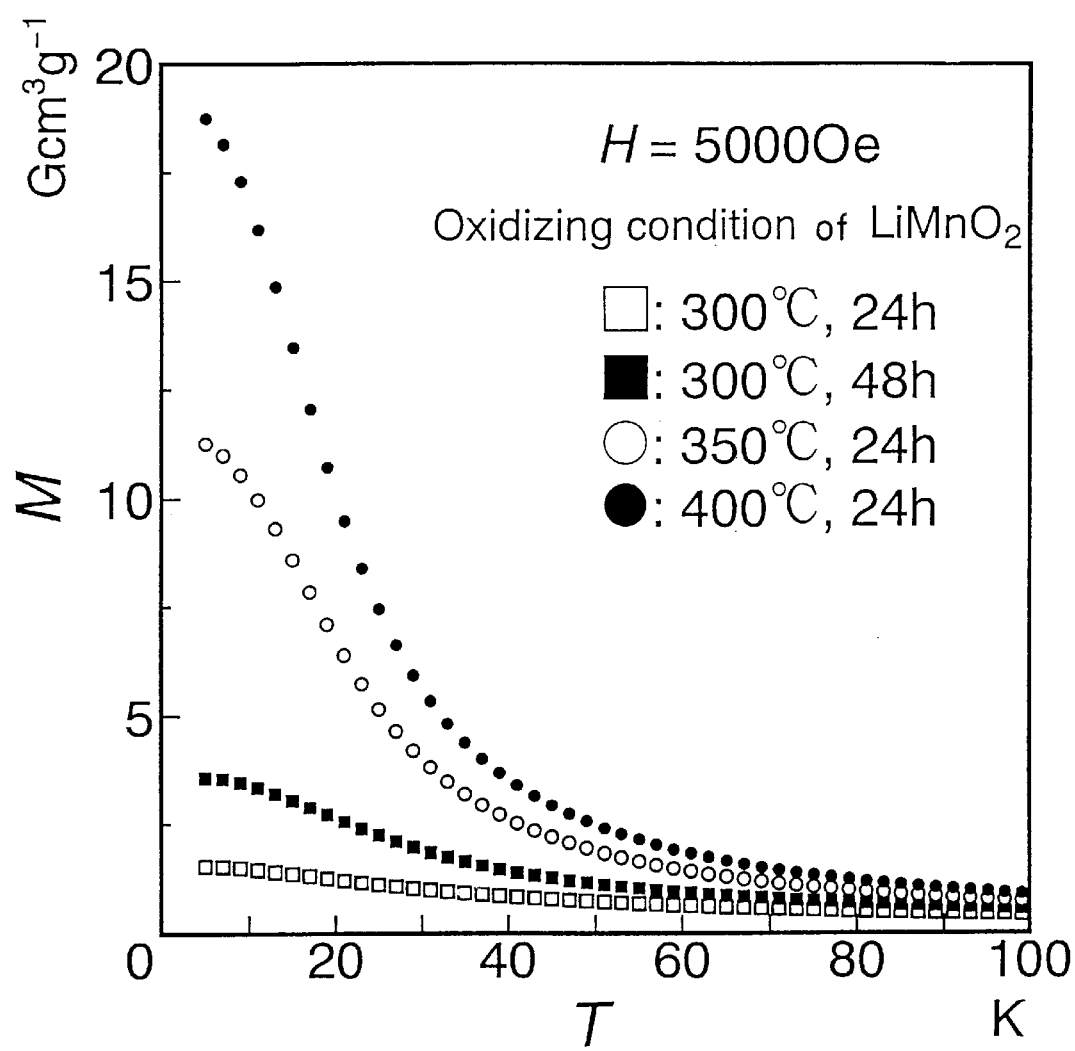
Figure 5:
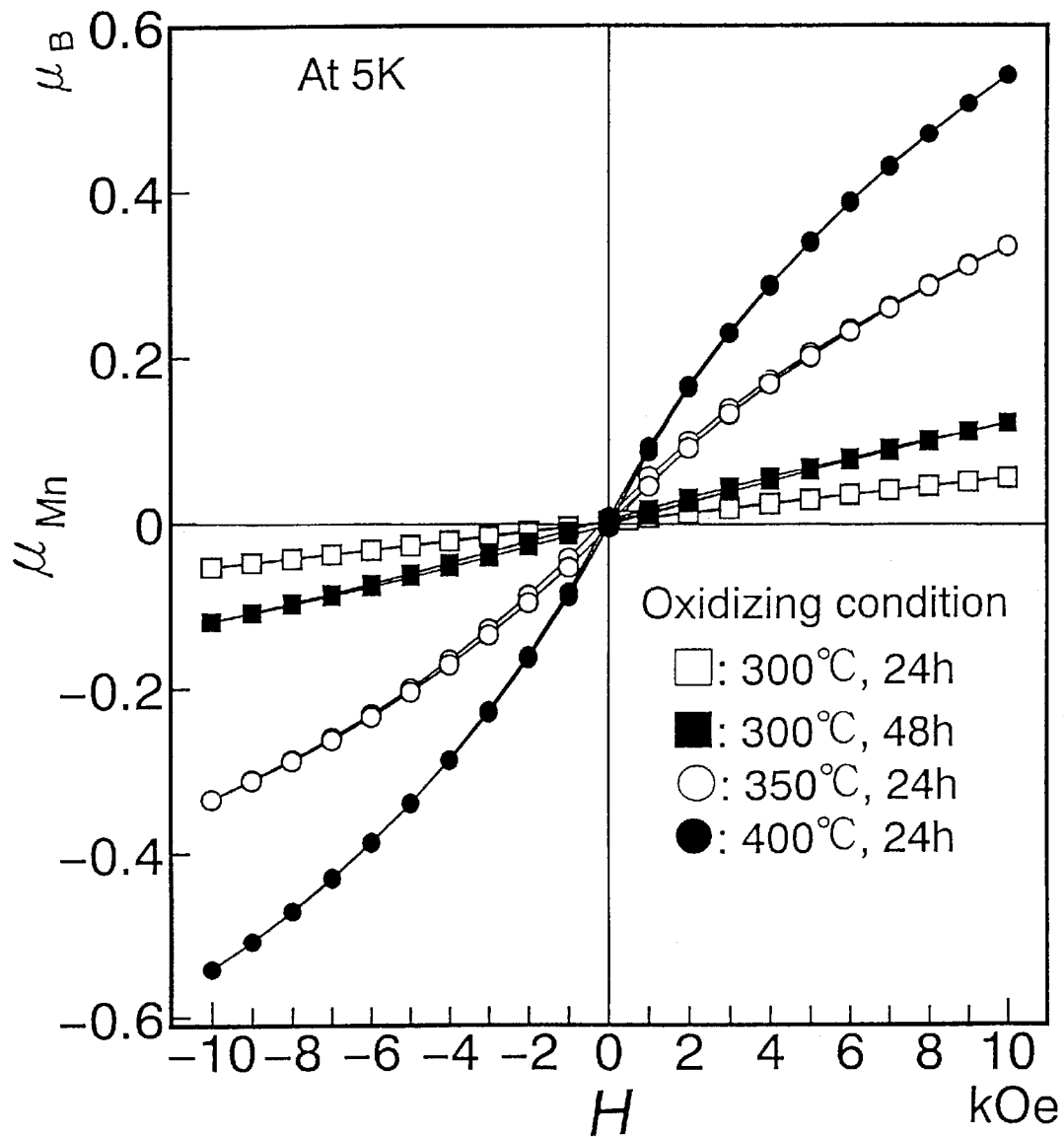
Figure 6:
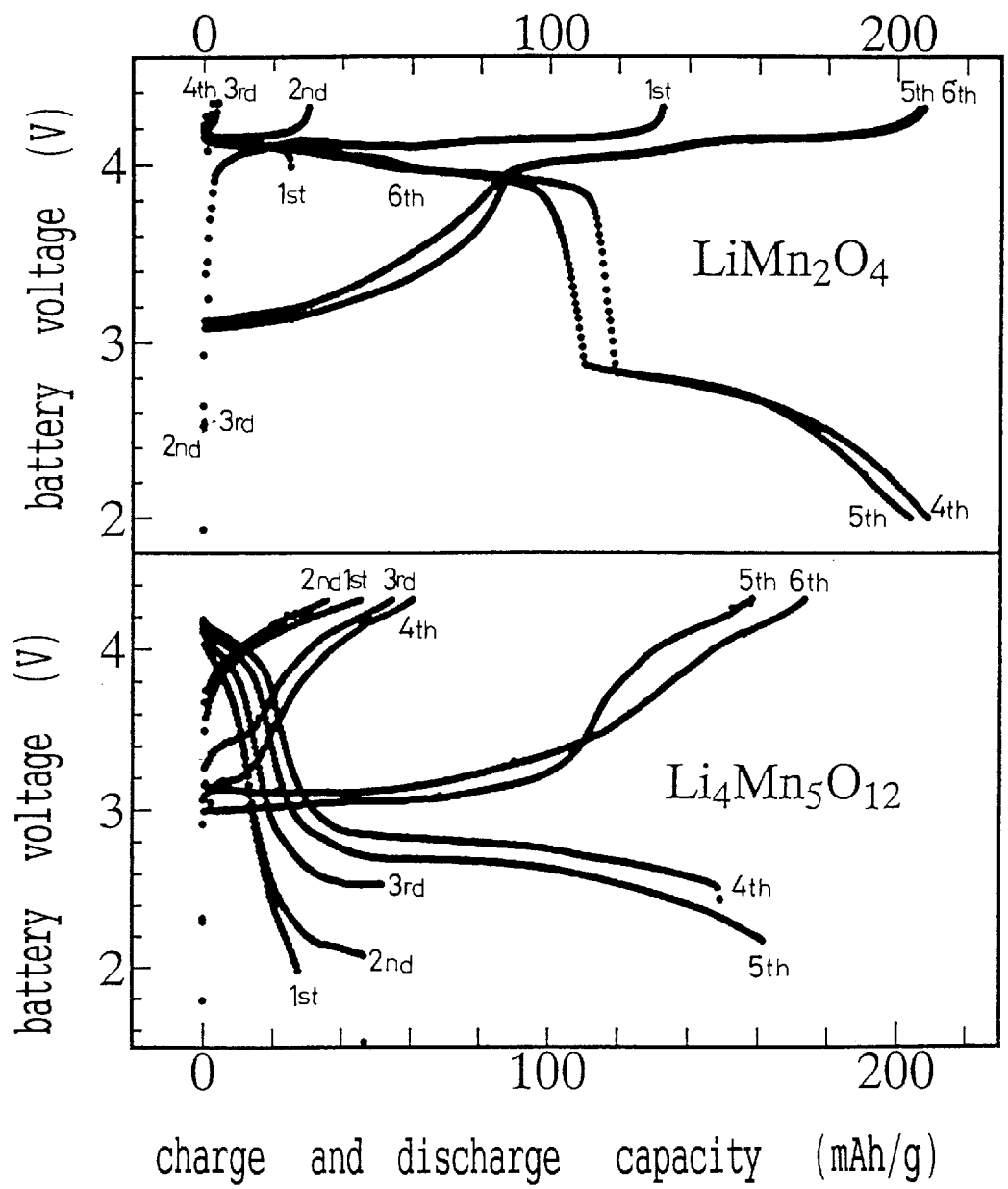

K for sample Nos. 1 to 4 prepared in Example 1, wherein the abscissa represents the measuring temperature with the ordinate representing the magnetic susceptibility per mol and the temperature, at which a linear approximate line represented by a broken line intersects the abscissa ($\chi_m^{-1}=0$) is Weiss temperature;

FIG. 4 is a graph showing the temperature dependency of magnetization for each oxidation conditions regarding sample Nos. 1 to 4 prepared in Example 1, wherein the abscissa represents the measuring temperature and the ordinate is the intensity of magnetization per g;

FIG. 5 is a graph showing the magnetic field dependency of magnetic moment (converted from magnetization) per Mn atom at 5 K for sample Nos. 1 to 4 prepared in Example 1;

FIG. 6 is a graph showing charge and discharge properties of a lithium rechargeable battery using two samples, prepared in Example 2, as a cathode material with Li as a counter electrode.

Figure 7:
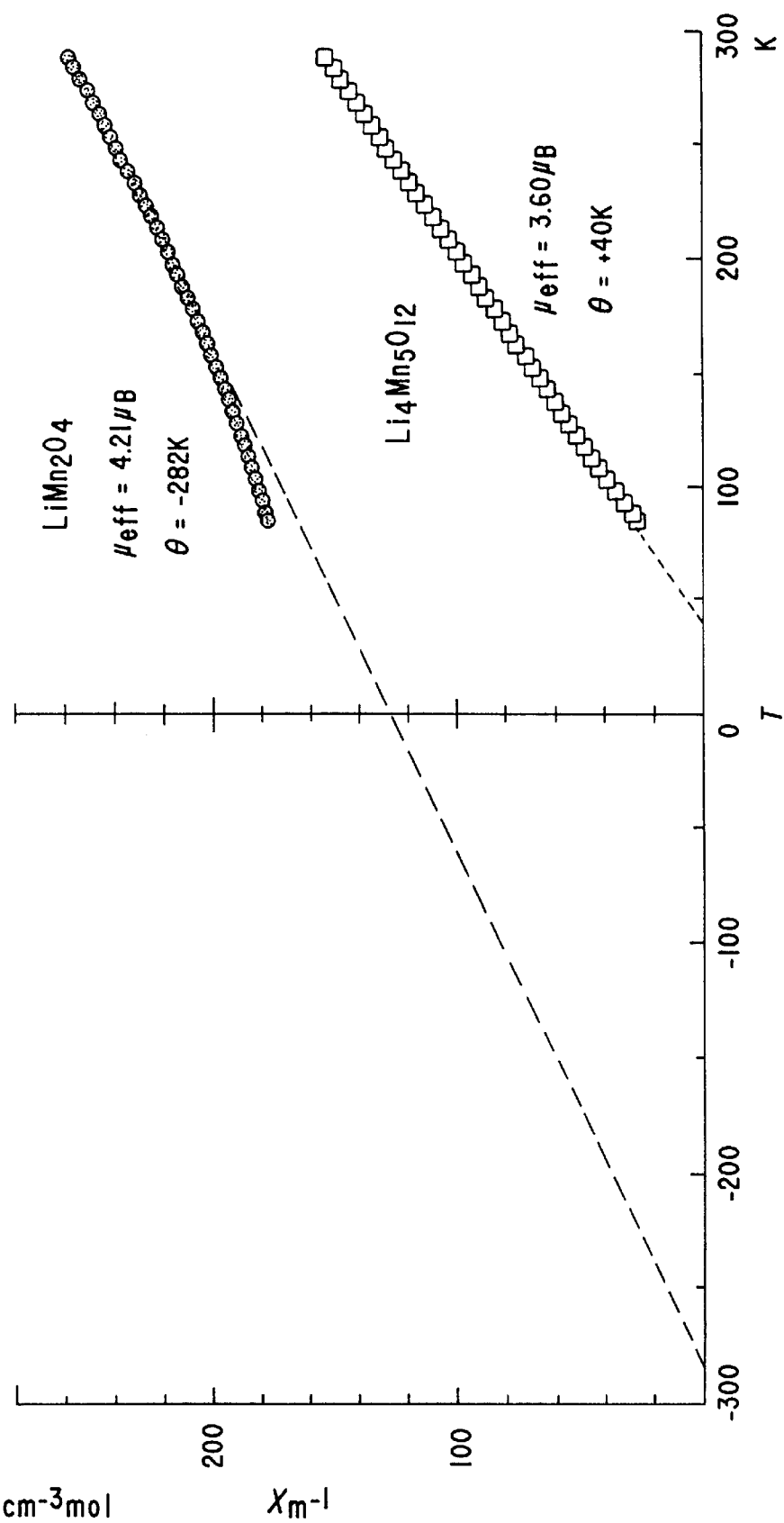

FIG. 7 is a graph showing the temperature dependency of the inverse number of the molar susceptibility for two samples prepared in Example 2.

Figure 8:
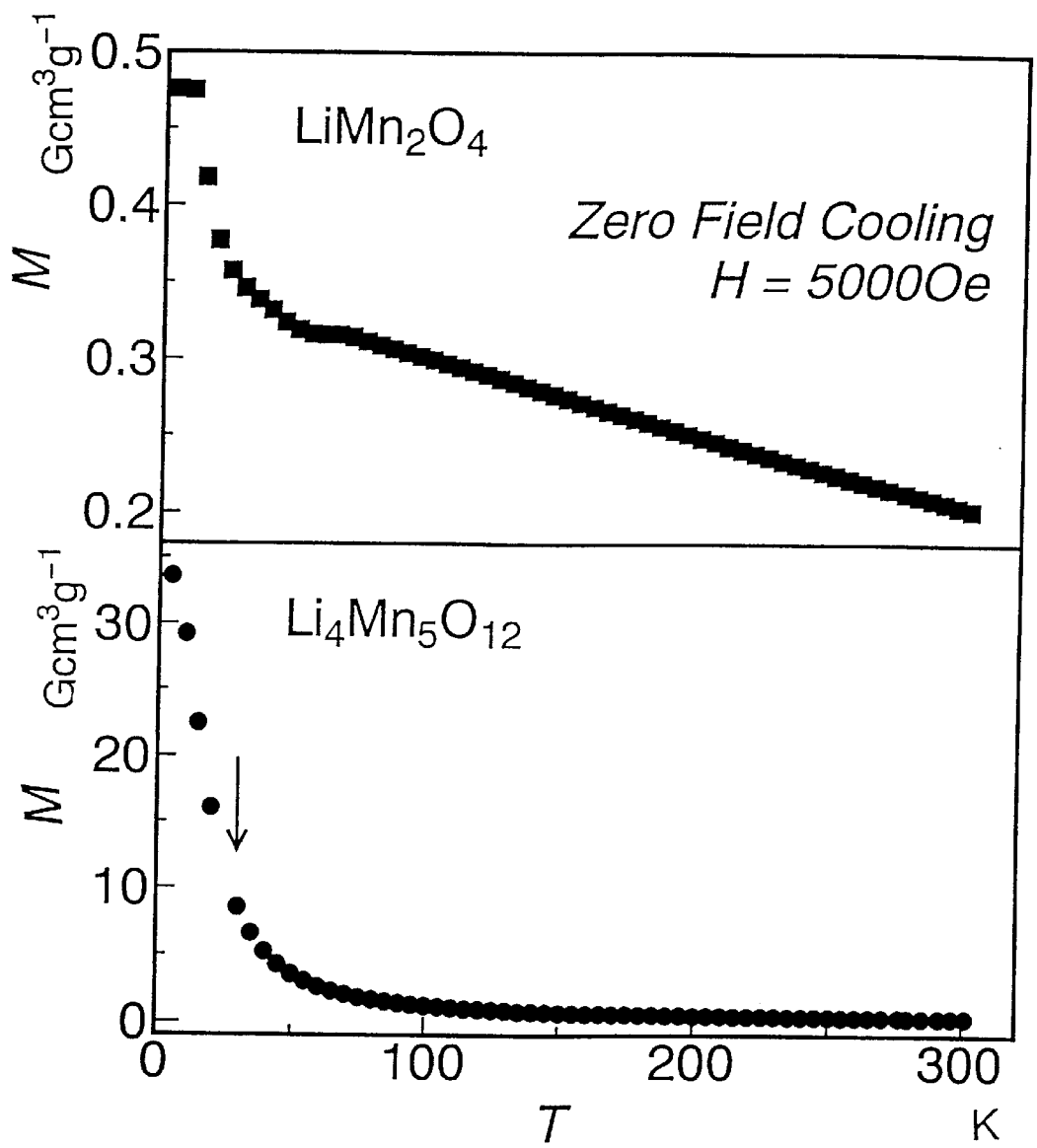
Figure 9:
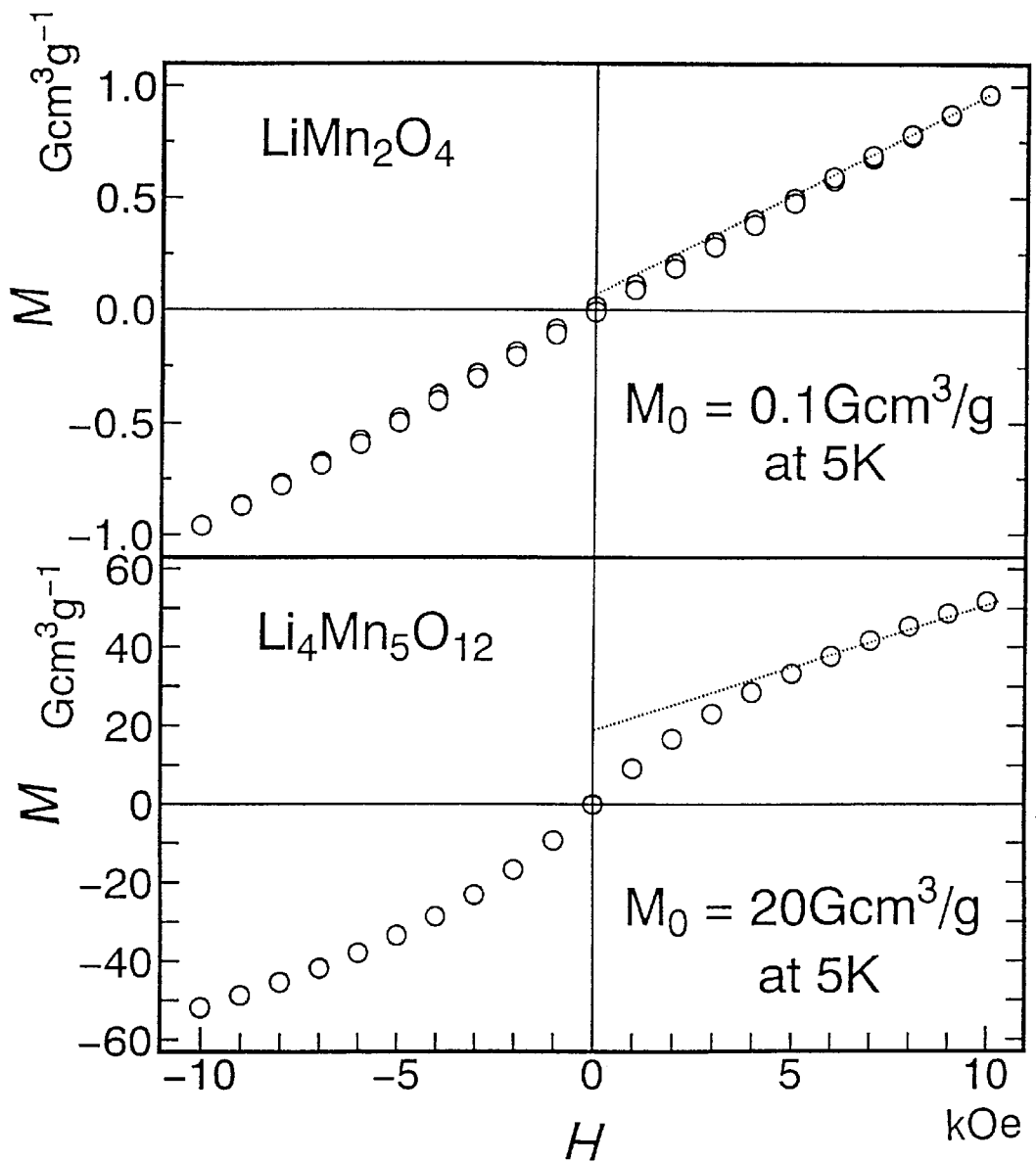

FIG. 8 is a graph showing the temperature dependency of magnetization per g of sample for two samples prepared in Example 2; and FIG. 9 is a graph showing the magnetic field dependency of magnetization per g of sample at 5 K for two samples prepared in Example 2.

DETAILED DESCRIPTION OF THE PREFERRED EMBODIMENT

The studies conducted by the present inventors have revealed that the inverse number ($\chi_m^{-1}$) of the molar susceptibility of lithium manganese spinels (such as $LiMn_2O_4$, $Li_2Mn_4O_9$, and $Li_4Mn_5O_{12}$) depends upon the temperature (T) and that the effective magnetic moment ($\mu_{eff}$) and Weiss temperature ($\theta$) provided by analyzing a linear portion, obtained from the above dependency, based on the Curie-Weiss' law ($\chi_m^{-1}=(T-\theta)/C_m$) depends upon the valency and distribution of Mn ion. Based on the above new finding, the present invention provides a method for predicting the charge and discharge capacities and operating voltage (4 V or 3 V) of a lithium rechargeable battery using a lithium manganese spinel as a cathode material.

The present inventors have further found that the behavior of the magnetic transition found in the temperature dependency of the magnetization (magnetic susceptibility) at 100 K or below for lithium manganese spinels (such as $LiMn_2O_4$, $Li_2Mn_4O_9$, and $Li_4Mn_5O_{12}$) depends upon the distribution and valency of Mn ion. The present invention, by taking advantage of this novel finding, provides a method for predicting the charge and discharge capacities and operating voltage (4 V or 3 V) as properties of a lithium rechargeable battery using a lithium manganese spinel as a cathode material.

The present invention will be described in more detail with reference to the accompanying drawings, if necessary.

For the synthesis of a lithium manganese spinel powder used in the evaluation of magnetic properties according to the present invention, there is no particular limitation on starting materials, conditions and the like. In general, however, the lithium manganese spinel powder may be synthesized as follows.

For example, a lithium manganese spinel (such as $LiMn_2O_4$, $Li_2Mn_4O_9$, or $Li_4Mn_5O_{12}$) can be prepared by providing one of various Mn compounds (such as manganese carbonate, manganese oxide, or manganese hydroxide oxide) and a Li compound (such as lithium carbonate, lithium hydroxide, or lithium nitrate) as starting compounds and conducting firing in air at about 300 to 1000° C.

Alternatively, the lithium manganese spinel (such as $LiMnO_{2+x}$) may be synthesized by low temperature (about 300 to 400° C.) oxidation of $LiMnO_2$ prepared by hydrothermally treating a manganese hydroxide oxide or manganese acetate with a large excess of a lithium hydroxide solution at 150 to 220° C.

A magnetic balance, wherein cooling and heating of a sample can be conducted, a superconducting quantum interference device (SQUID) and the like may be used as a device for evaluating the magnetic properties. Most preferably, the device can cover the measuring temperature range of from room temperature to liquid helium temperature. However, a device which permits cooling to a liquid nitrogen temperature can also be used so far as data on the temperature dependency of the magnetic susceptibility can be obtained.

The sample may be in a powdery form and is not required to be sintered. The amount of the sample may generally be not more than 100 mg although it may vary depending upon the material.

Numerical values necessary for interpreting the results of the magnetic measurement are only the amount of the sample and the content of manganese in the sample.

Prior to the measurement of the magnetic susceptibility, in order to examine the presence or absence of ferromagnetic impurities, it is preferred to determine the magnetic field dependency of magnetization at room temperature, liquid nitrogen temperature and the like.

The present invention will be described in more detail by taking $LiMn_2O_4$, a kind of lithium manganese spinel, as an example.

In the case of a lithium rechargeable battery with $LiMn_2O_4$ as the cathode, the insertion of Li into $LiMn_2O_4$ causes the valency of Mn to change from 3.5 toward 3. On the other hand, the extraction of Li causes the valence of Mn to change from 3.5 toward 4. Therefore, charge and discharge properties of a lithium rechargeable battery are sensitive to a change in the valency of the transition metal ion in the cathode. Further, for the lithium manganese spinel, many crystalline phases exist depending upon the ion distribution of Mn, Li/Mn ratio, and the amount of cation vacancy. For example, $Mn^{4+}$ spinels, such as $Li_2Mn_4O_9$ and $Li_4Mn_5O_{12}$, cannot electrochemically extract Li ion and exhibit 3 V plateau voltage only.

Most of $Mn^{3+}$ and $Mn^{4+}$ ions in the lithium manganese spinel situated in six-coordinate position, and the theoretical value of the effective magnetic moment ($\mu_{eff}$) determined from the temperature dependency of the magnetic susceptibility is expected to be 4.9 $\mu_B$ for $Mn^{3+}$ ion (high-spin state) and 3.8 $\mu_B$ for $Mn^{4+}$ ion. Therefore, since the valency of Mn ion contained in the spinel structure can be quantitatively estimated by experimental determination of the effective magnetic moment, the charge and discharge capacities and operating voltage can be simply expected in a powdery form by utilizing the evaluation of magnetic properties. Further, since the magnetic interaction, between manganese ions (which reflects the Weiss temperature ($\theta$)) varies depending upon the valency of manganese, a combination of two parameters enables a lithium manganese spinel cathode material constituting the battery to be evaluated in a raw material state.

Therefore, combining a cathode material, selected based on this evaluation, with an electrolyte and a negative electrode can contribute greatly to the optimization of the properties of the battery.

According to the present invention, the charge and discharge capacities and the operating voltage of a lithium rechargeable battery using a lithium manganese spinel as the cathode material can be simply predicted by magnetically evaluating a lithium manganese spinel powder.

Features of the present invention will be described in more detail with reference to the following examples and test examples.

The crystalline phase and the chemical composition of samples applied to the magnetic measurement were evaluated by the X-ray diffractometry and chemical analysis (the determination of Li by the atomic absorption method and the determination of the valency of manganese by redox titration).

EXAMPLE 1

Figure 1:
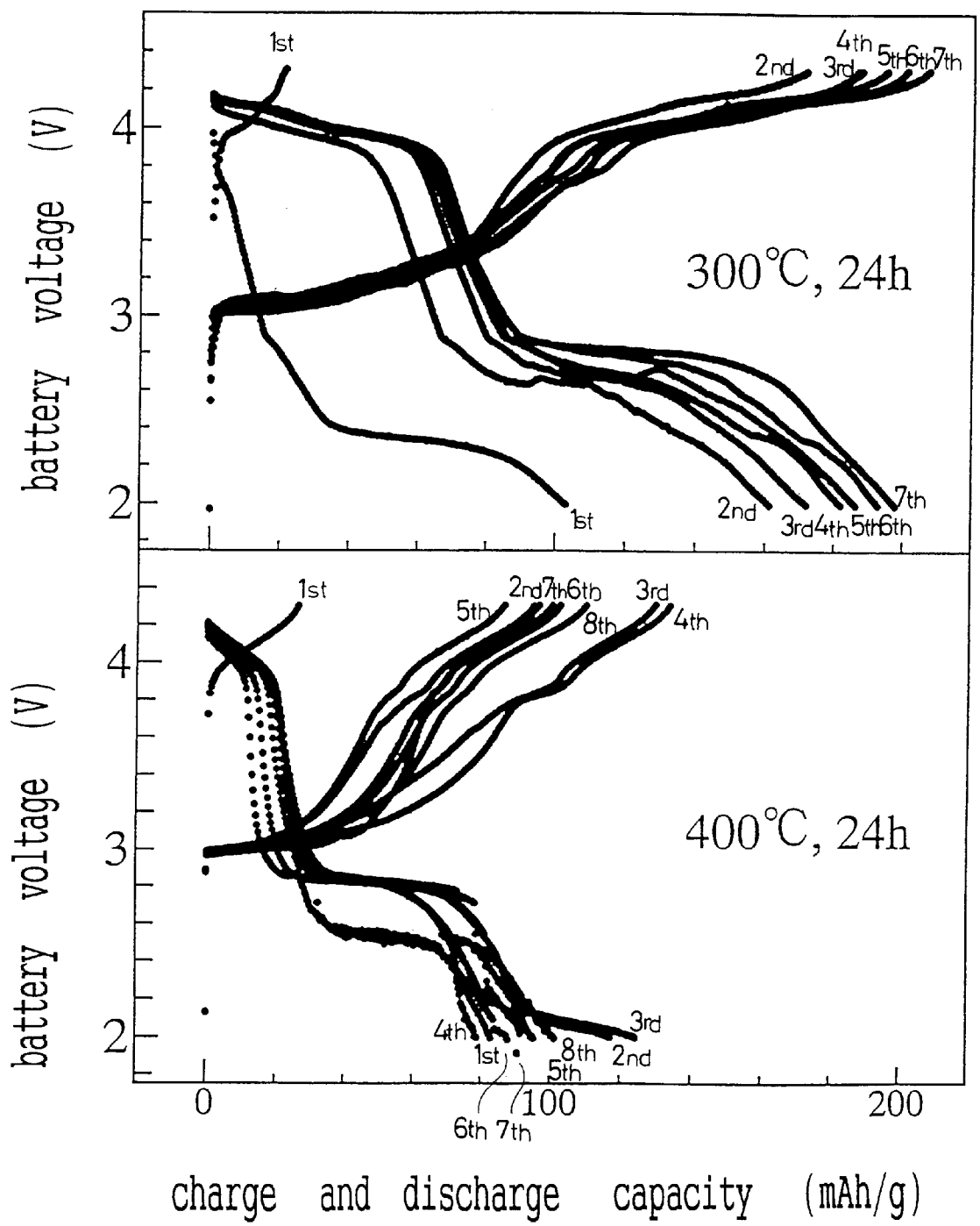
FIG. 1 is a graph showing charge and discharge properties of a lithium rechargeable battery using sample No. 1 or No. 3, prepared in Example 1 as a cathode material with Li as a counter electrode.

Four lithium manganese spinel Nos. 1 to 4 prepared by firing hydrothermally synthesized $LiMnO_2$ at 300° C., 350° C., or 400° C. for 24 hr or 48 hr were evaluated for magnetic properties. For the above materials, compositions ($LiMno_{2+x}$) and the like are tabulated in Table 1, and the analysis by X-ray diffraction revealed that all the materials were in the form of a single phase.

that, at least at this temperature or above, the magnetic susceptibility may be determined by (measured magnetization)/(magnetic field). Each curve shown in FIG. 1 shows the results of repetition of charge and discharge seven times from the initial charge and discharge. The number given to each curve represents the order of charge and discharge. For each drawing, m represents that the value is one per mole.

Figure 3:
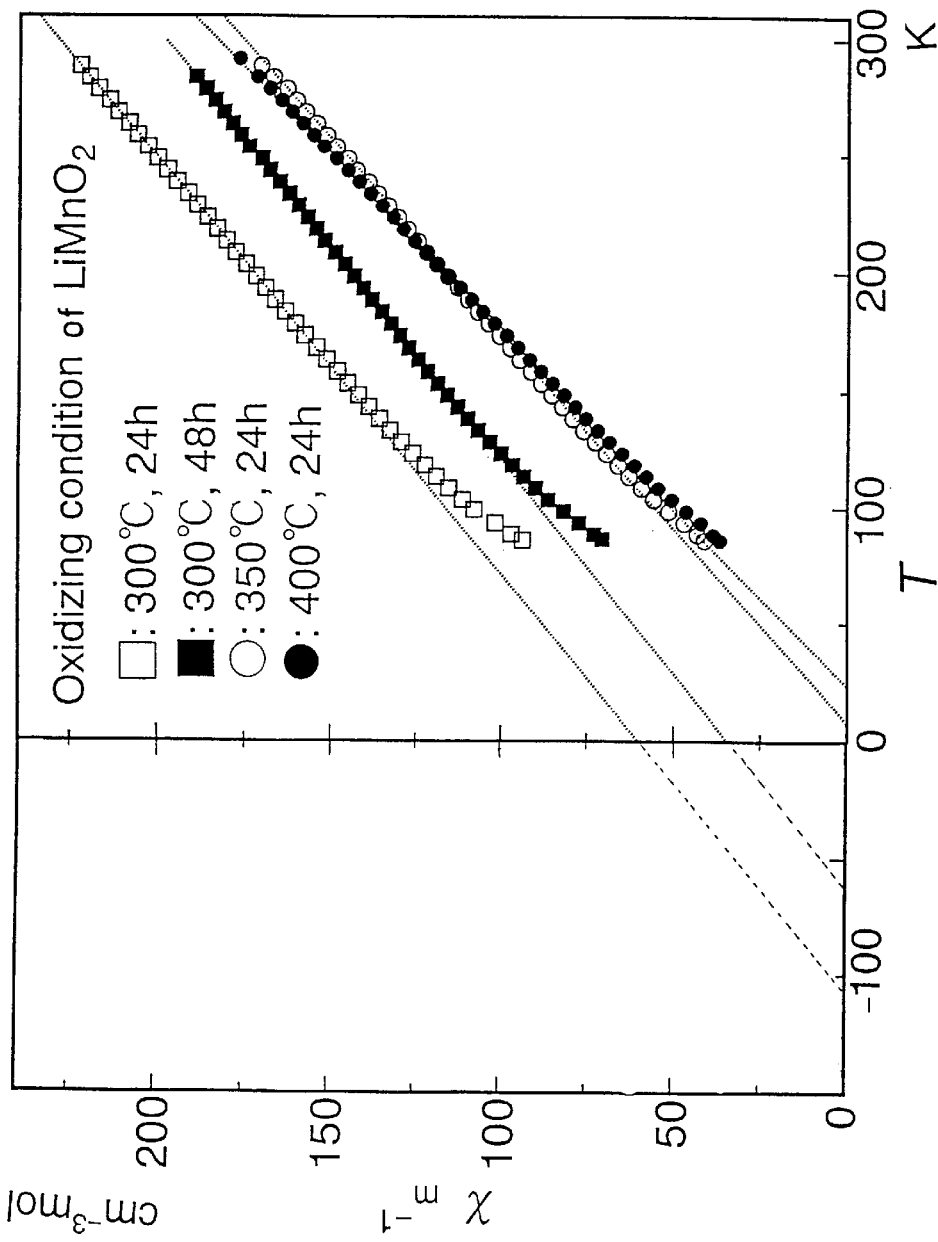
FIG. 3 is a graph showing the temperature dependency of the inverse number of the molar susceptibility at 83 to 300

Further, data on the temperature dependency of the inverse number of the molar susceptibility for each sample at 83 K to 300 K are shown in FIG. 3. From FIG. 3, it is apparent that each of sample Nos. 1 to 4 can be linearly approximated at 120 K or more and analyzed based on the Curie-Weiss' law ($\chi_m^{-1}=(1/C_m)\times(T-\theta)$). That the samples are different from one another in slope of the straight line (square root of the inverse number being proportional to the effective magnetic moment) and temperature at $\chi_m^{-1}=0$ (corresponding to the Weiss temperature) corresponds to that situation in which the samples are different from one another in the valency state of Mn ion and interaction between the ions. The effective magnetic moment ($\mu_{eff}$), the Weiss temperature ($\theta$) and the magnetic moment ($\mu_{Mn}$) at 5 K, determined by this linear approximation, are tabulated in Table 2.

TABLE 1

| Sample | Oxidizing conditions | Li (wt %) | Valency of Mn | Li:Mn atomic ratio | O:Mn atomic ratio |
|---|---|---|---|---|---|
| $LiMnO_2$ (Hydrothermally synthesized | — | 7.40 ± 0.06 | 3.04 | 1.01 ± 0.01 | 2.02 ± 0.01 |
| No. 1 Spinel (T Phase) | 300° C. 24 hr | 7.25 ± 0.09 | 3.43 | 1.02 ± 0.01 | 2.23 ± 0.02 |
| No. 2 Spinel (C phase) | 350° C. 24 hr | 6.92 ± 0.12 | 3.65 | 0.99 ± 0.02 | 2.32 ± 0.03 |
| No. 3 Spinel (C phase) | 400° C. 24 hr | 6.86 ± 0.13 | 3.79 | 0.99 ± 0.02 | 2.39 ± 0.03 |
| No. 4 Spinel (C phase) | 300° C. 48 hr | 6.80 ± 0.04 | 3.72 | 0.97 ± 0.01 | 2.35 ± 0.01 |

Note: $LiMnO_2$ listed on the uppermost row in the column of "Sample" is a material, per se, which has been synthesized by a hydrothermal process.
T phase: Tetragonal
C phase: Cubic The above four lithium manganese spinel samples are novel compounds prepared by combining the hydrothermal process with the low temperature oxidation and are substantially identical in Li/Mn ratio with the valency of Mn alone being different, rendering these samples suitable for the present invention.

FIG. 1 is a graph showing charge and discharge properties of a lithium rechargeable battery wherein sample No. 1 or No. 4, which has been subjected to low temperature oxidation at 300° C. or 400° C. for 24 hr, among the four samples is used as a cathode material with Li as a counter electrode.

Figure 2:
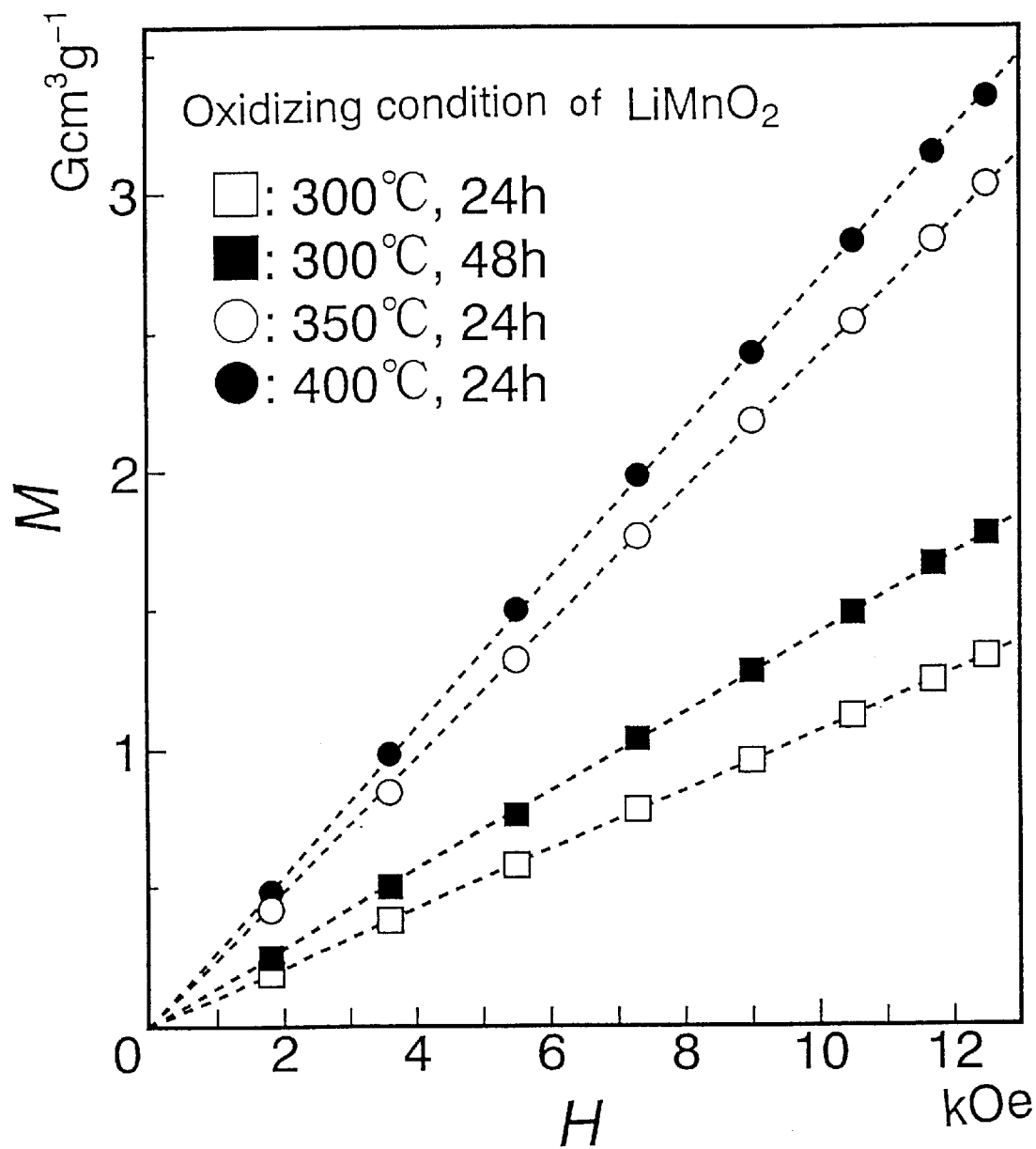
FIG. 2 is a graph showing the dependency of magnetization at 83 K on the-magnetic field for sample Nos. 1 to 4 prepared in Example 1, wherein the abscissa represents the magnetic field and the ordinate is the intensity of magnetization per g.

It can be understood that both the batteries are greatly different from each other in the charge and discharge capacities from 4.3 to 3 V and the plateau voltage (operating voltage). In order to elucidate the cause, the magnetic measurement was performed for each sample. Data on the magnetic field dependency of magnetization for each sample at 83 K are shown in FIG. 2. For all the samples, the plot has a positive slope, and linear approximation is possible with the intercept of the magnetization axis being zero, indicating

TABLE 2

| Sample | $\mu_{eff}/\mu_B$ | $\theta$ (K) | $\mu_{Mn}$ at 5 K |
|---|---|---|---|
| No. 1 | 3.667 (8) | −98 (1) | <0.01 |
| No. 2 | 3.629 (5) | +6.1 (7) | 0.098 |
| No. 3 | 3.472 (3) | +24.5 (4) | 0.19 |
| No. 4 | 3.805 (3) | −62 (1) | 0.017 |

Note: For sample No. 1 listed in Table 2, a $\mu_{eff}/\mu_B$ value of "3.667 (8)" means "3.667 ± 0.008," and a $\theta$ (K) value of "−98 (1)" means "−98 ± 1." These are true of sample Nos. 2 to 4.

The relationship, between the effective magnetic moment and Weiss temperature and the oxidation temperature and valency of Mn, determined from the comparison of Table 1 with Table 2 is shown in Table 3.

TABLE 3

| Sample | Oxidizing conditions Temp. | Time | Valency of Mn | $\mu_{eff}/\mu_B$ | θ (K) |
|---|---|---|---|---|---|
| No. 1 | 300° C. | 24 h | 3.43 | 3.667 (8) | −98 (1) |
| No. 2 | 350° C. | 24 h | 3.65 | 3.629 (5) | +6.1 (7) |
| No. 3 | 400° C. | 24 h | 3.79 | 3.427 (3) | +24.5 (4) |
| No. 4 | 300° C. | 48 h | 3.72 | 3.805 (3) | −62 (1) |

As can be understood from Table 3, the valency of Mn and the effective magnetic moment decrease with increasing the oxidizing temperature, and the Weiss temperature continuously changes from a negative value to a positive value with increasing the oxidizing temperature. For the correlation between the effective magnetic moment and the valency of Mn shown in Table 3, data for sample Nos. 1 to 3 show a tendency different from data for sample No. 4. Analysis by X-ray diffractometry has revealed that this is attributable to the fact that the lattice volume of Mn for sample No. 4 is different from that of Mn for sample Nos. 1 to 3. In both cases of the determination of the above correlation and the prediction, it is preferred to simultaneously measure the lattice volume of Mn.

The change in effective magnetic moment can be interpreted as a change of a part of high-spin $Mn^{3+}$ (number of unpaired 3d electrons: 4, expected effective magnetic moment: 4.9 $\mu_B$) ion, substantially 100% of which has been contained in the $LiMnO_2$ sample before the oxidation, to $Mn^{4+}$ (number of unpaired 3d electrons: 3, expected effective magnetic moment: 3.8 $\mu_B$) ion. This indicates that the amount of high-spin $Mn^{3+}$ decreases with increasing the oxidizing temperature, which is in agreement with the results of chemical analysis (Table 1). Further, in the charge and discharge curve shown in FIG. 1, the plateau capacity around 4 V is said to be created by a change from $Mn^{3+}$ to $Mn^{4+}$ accompanying the extraction of Li which occupies the four-coordinate position of the oxide ion in the crystal structure. This means that the capacity for the sample oxidized at 300° C. is larger than that for the sample oxidized at 400° C., which is in agreement with the results of the magnetic measurement and the results of chemical analysis.

On the other hand, a continuous change in Weiss temperature from a negative value to a positive value with increasing the firing temperature indicates that the interaction between Mn ions at 83 K or below changes from antiferromagnetic interaction to ferromagnetic interaction. With this, the magnetization at 50 K or below rapidly increases (see FIG. 4 showing the relationship between oxidizing conditions and magnetization for sample Nos. 1 to 4), and, from the data on the magnetic field dependency of the magnetic moment (converted from the spontaneous magnetization) created per Mn atom at 5 K (see FIG. 5), this increase could be found to be attributable to the creation of spontaneous magnetization. The relationship between the resultant spontaneous magnetization and the oxidizing conditions and valency of Mn is tabulated in Table 4.

TABLE 4

| Sample | Oxidizing Conditions Temp | Time | Valency of Mn | $\mu_{Mn}/\mu_B$ | lattice volume |
|---|---|---|---|---|---|
| No.1 | 300° C. | 24 h | 3.43 | <0.01 | 549.893Å³ |
| No.2 | 350° C. | 24 h | 3.65 | 0.098 | 545.739Å³ |
| No.3 | 400° C. | 24 h | 3.79 | 0.19 | 542.540Å³ |
| No.4 | 300° C. | 48 h | 3.72 | 0.017 | 552.175Å³ |

In the above Table 4, "$\mu_{Mn}/\mu_B$" represents the magnetic moment, per Mn atom, converted from the spontaneous magnetization. Also in the Table, the Samples No. 3 and 4 have closely resembling values for the Valency of Mn, but their respective values for the magnetic moment, $\mu_{Mn}/\mu_B$, and the lattice volume are relatively largely different from each other, so that in predicting battery characteristics, preferably determination of the lattice volume should be made as well as other factors.

This also means that, as previously reported by Blasse (G. Blasse, J. Phys. Chem. Solids. Vol. 27 (1966), pp. 383–389), the ferromagnetic interaction between $Mn^{4+}$ ions at the position of the octahedron in the spinel structure through the oxide ion increases with increasing the firing temperature, which is in agreement with the results of the effective magnetic moment.

The relationship between measured values of the charge and discharge capacities and operating voltage for sample Nos. 1 to 4 (the results of measurement for sample Nos. 1 and 2 being shown in FIG. 1) and the effective magnetic moment, Weiss temperature, and spontaneous magnetization are tabulated in Table 5.

TABLE 5

| Sample | $\mu_{eff}/\mu_B$ | θ (K) | Converted from Spontaneous magnetization $\mu_{Mn}/\mu_B$ | Charge and discharge capacity (mAh/g) | Operating voltage (V) |
|---|---|---|---|---|---|
| No. 1 | 3.667 (8) | −98 (1) | <0.01 | 160–200 | 4 and 3 |
| No. 2 | 3.629 (5) | +6.1 (7) | 0.098 | — | — |
| No. 3 | 3.472 (3) | +24.5 (4) | 0.19 | 80–120 | mainly 3 |
| No. 4 | 3.805 (3) | −62 (1) | 0.017 | — | — |

As is apparent from the results shown in Table 5, the lithium manganese spinel cathode material constituting the battery can be evaluated in a raw material state by determining the relationship between the spontaneous magnetization and charge and discharge capacities (having a correlation with the valency of Mn) and the effective magnetic moment, Weiss temperature, and spontaneous magnetization and, for a known sample, previously determining the relational expressions for each relationship.

EXAMPLE 2

Lithium manganese spinels, $LiMn_2O_4$ and $Li_4Mn_5O_{12}$, prepared by providing starting compounds, i.e., manganese hydroxide oxide as a Mn source and lithium hydroxide monohydrate as a Li source, and conducting sintering in air at 300 to 1000° C. were used as samples for measurement in each test ($LiMn_2O_4$ and $Li_4Mn_5O_{12}$ having been confirmed, by chemical analysis and X-ray diffractometry, to be in the form of a single phase).

Charge and discharge properties of lithium rechargeable batteries using two samples as a cathode material with Li as a counter material are shown in FIG. 6. As described above, there is a difference, in operating voltage and charge and discharge capacities, reflecting the fact that the valency of Mn in $LiMn_2O_4$ is 3.5 and that of $Li_4Mn_5O_{12}$ is 4.0.

As is apparent from the data on the magnetic field dependency of the magnetization at 83 K for these samples, as with Example 1, the development of spontaneous magnetization does not occur. The data on the temperature dependency of the inverse number of the molar magnetic susceptibility for each sample at 83 to 300 K are shown in FIG. 7. FIG. 7 shows that for both samples, linear approximation is possible at 150 K or more, and analysis can be made based on the Curie-Weiss' law ($\chi_m^{-1}=(1/C_m)\times(T-\theta)$). The effective magnetic moment shows that $LiMn_2O_4$ is a compound having a mixed valency of a high-spin $Mn^{3+}$ (number of unpaired 3d electrons: 4, expected effective magnetic moment: 4.9 $\mu_B$) ion and $Mn^{4+}$ (number of unpaired 3d electrons: 3, expected effective magnetic moment: 3.8 $\mu_B$) ion and that $Li_4Mn_5O_{12}$ consists essentially of $Mn^{4+}$ alone. This is in agreement with the results of the chemical analysis.

Further, the temperature dependency of the magnetization at 5 to 300 K (see FIG. 8) and the magnetic field dependency of the magnetization at 5 K (FIG. 9) show that, as described above, regarding the difference in Weiss temperature between both samples, contribution of the interaction between $Mn^{4+}$ ions through the oxide ion in $Li_4Mn_5O_{12}$ as a $Mn^{4+}$ compound is greater than that in $LiMn_2O_4$.

For Example 2, data corresponding to the data given in Table 5 in Example 1 are tabulated in Table 6.

TABLE 6

| Sample | $\mu_{eff}/\mu_B$ | θ (K) | Spontaneous magnetization M (Gcm³/g) | Charge and discharge capacity (mAh/g) | Operating voltage (V) |
| --- | --- | --- | --- | --- | --- |
| No. 5 | 4.21 | −282 | 0.1 | 200 | 4 and 3 |
| No. 6 | 3.60 | +40 | 20 | 160 | mainly 3 |

Thus, the application of the method of the present invention to a lithium manganese spinel enables the capacity and the operating voltage on charge and discharge properties of a lithium rechargeable battery using the lithium manganese spinel as a cathode to be predicted in a solid powder in a simple manner.

What is claimed is:

1. A method of determining the charge and/or discharge capacities of non-aqueous batteries with an operating voltage of about 4 volts, comprising:
   determining an inverse molar susceptibility value at each of a plurality of different temperatures for a plurality of lithium manganese spinel oxide cathode materials having different respective Mn valencies;
   plotting the inverse molar susceptibility values against temperatures for each of the plurality of lithium manganese spinel oxide cathode materials;
   determining values of at least one of two paramagnetic parameters, Weiss temperature and effective magnetic moment, by obtaining the temperature dependence of the above inverse molar susceptibility from a plot derived from the Curie-Weiss law, said Weiss temperature corresponding to a temperature value extrapolated to a zero point of the inverse molar susceptibility and said effective magnetic moment being obtainable from the gradient value of the plot;
   producing plural rechargeable lithium batteries in which lithium manganese spinel oxides with well-defined Mn valencies are used as cathode materials, and finding at least one of the charge or discharge capacities around 4 V for each of the batteries;
   providing at least one correlation curve between the above-found charge and/or discharge capacities and the above-found at least one paramagnetic parameter value; and
   obtaining charge and/or discharge capacities for a rechargeable lithium battery containing a lithium manganese spinel oxide whose charge and/or discharge capacities are being sought from said at lest one determined paramagnetic parameter value using said at least one correlation curve.

2. A method of determining the charge and/or discharge capacities of non-aqueous batteries with an operating voltage of about 4 volts, comprising:
   determining a spontaneous magnetization value for each of a plurality of lithium manganese spinel oxide cathode materials having a different respective Mn valency by determining a magnetization value of each of a plurality of magnetic fields at a constant temperature, plotting the determined magnetization values against the magnetic fields and extrapolating the magnetization values to zero magnetic field based on the resulting plot;
   determining the charge and/or discharge capacities around 4 V of rechargeable lithium batteries in which lithium manganese spinel oxides having well-defined Mn valencies are used as cathode materials;
   obtaining at least one correlation curve by plotting values of said charge and/or discharge capacities around 4 V versus said spontaneous magnetization values obtained by extrapolating to zero magnetic field as a linear function of magnetic field;
   obtaining the spontaneous magnetization value at each of said plurality of different magnetic fields at said constant temperature in connection with a lithium manganese spinel oxide with a Mn valency being sought; and
   obtaining the charge and/or discharge capacities for a rechargeable lithium battery containing said lithium manganese spinel oxide having a Mn valency being sought corresponding to said spontaneous magnetization values obtained by using said correlation curve.

3. A method of determining the charge and/or discharge capacities of non-aqueous batteries with an operating voltage of about 4 volts according to claim 1, wherein inverse molar susceptibility values are determined at temperatures between 83 and 300° K.

4. A method of determining the charge and/or discharge capacities of non-aqueous batteries with an operating voltage of about 4 volts according to claim 2, wherein spontaneous magnetization values are determined within a range from 5 to 83° K.

* * * * *